United States Patent [19]

van Lintel

[11] Patent Number: 5,219,278

[45] Date of Patent: Jun. 15, 1993

[54] MICROPUMP WITH IMPROVED PRIMING

[75] Inventor: Harald T. G. van Lintel, Enschede, Netherlands

[73] Assignee: Westonbridge International, Ltd., Dublin, Ireland

[21] Appl. No.: 689,259

[22] PCT Filed: Nov. 7, 1990

[86] PCT No.: PCT/EP90/01861

§ 371 Date: Sep. 4, 1991

§ 102(e) Date: Sep. 4, 1991

[87] PCT Pub. No.: WO91/07591

PCT Pub. Date: May 30, 1991

[30] Foreign Application Priority Data

Nov. 10, 1989 [CH] Switzerland ............ 04055/89
Mar. 5, 1990 [CH] Switzerland ............ 00694/90

[51] Int. Cl.$^5$ .................................. F04B 43/04
[52] U.S. Cl. .................................. 417/413 R
[58] Field of Search ............... 417/410, 413, 322

[56] References Cited

U.S. PATENT DOCUMENTS

| | | | |
|---|---|---|---|
| 3,150,592 | 9/1964 | Stec | 417/322 |
| 3,215,078 | 11/1965 | Stec | 417/322 |
| 4,708,600 | 11/1987 | AbuJudom, II et al. | 417/322 |
| 4,911,616 | 3/1990 | Laumann, Jr. | 417/413 |
| 4,938,742 | 7/1990 | Smits | 417/322 X |
| 4,939,405 | 7/1990 | Okuyama et al. | 417/410 X |

FOREIGN PATENT DOCUMENTS

| | | | |
|---|---|---|---|
| 0134614 | 3/1985 | European Pat. Off. | 417/413 |
| 0322899 | 7/1989 | European Pat. Off. | 417/413 |
| 0392978 | 10/1990 | European Pat. Off. | |
| 61-171891 | 8/1986 | Japan | 417/413 |
| WO9015929 | 12/1990 | World Int. Prop. O. | 417/322 |

OTHER PUBLICATIONS

Article entitled "A piezoelectric micropump based on micromachining of silicon" *Sensors and Actuators*, No. 15 (1988) pp. 153-167 by H. T. van Lintel, et al.
International Search Report of International Application No. PCT/EP90/01861.
Copending U.S. application Ser. No. 07/503,977 filed Apr. 4, 1990.

*Primary Examiner*—Leonard E. Smith
*Attorney, Agent, or Firm*—Pollock, Vande Sande & Priddy

[57] ABSTRACT

The micropump comprises a silicon wafer (22), glass wafers (2, 24) and a control element (26). The wafer (22) is machined to define an inlet valve (36), a pump chamber (34) and an outlet valve (48). The inlet valve (36) comprises a membrane (40) defining an upstream compartment (38) and a downstream compartment (62), an orifice (42) and a sealing ring (46) surrounding this orifice. The orifice (42) is pierced at a location in such a way that, during the priming of the micropump, the fluid arriving in the downstream compartment reaches a specific and unique part (60) of the downstream compartment wall before reaching other parts of the wall. The fluid is then propelled along the wall on both sides of the part (60) by pushing the air away ahead of it and thus guaranteeing that no air bubble can be formed in the downstream compartment.

15 Claims, 5 Drawing Sheets

MICROPUMP WITH IMPROVED PRIMING

The present invention relates to micropumps, and particularly to micropumps in which at least part of the pump mechanism is made by machining a wafer using micromachining technologies such as photolithographic technology. More specifically, it relates to a micropump structure having improved priming.

BACKGROUND OF THE INVENTION

Pumps of this type can be used notably for the in situ administration of medicaments whereby miniaturization of the pump enables the patient to wear it on his person or possibly to have a pump directly implanted in his body. In addition, using pumps of this type, small quantities of liquid to be injected can be accurately administrated.

In an article entitled "A piezoelectric micropump based on micromachining of silicon" published in "Sensors and Actuators" No. 15 (1988), pages 153 to 167, H. van Lintel et al describe two embodiments of a micropump each comprising a stack of three wafers, i.e. a wafer of machined silicon arranged between two wafers of glass.

The silicon wafer defines a pump chamber with one of the glass wafers, it being possible for the part coinciding with this chamber to be deformed by drive means, in the present case a piezoelectric crystal. The latter comprises electrodes which, when connected to an alternating voltage source, cause deformation of the crystal and thus of the glass wafer, the latter in turn causing variation in the volume of the pump chamber.

The pump chamber is connected on each side to check valves machined from silicon the seat of which is composed of the other glass wafer.

The mode of operation of this type of pump is influenced by the compressibility of the fluid and it may consequently not work if it contains too much air.

Various techniques exist for priming these micropumps.

According to a first technique, priming occurs under vacuum. The inlet of the micropump is linked to a fluid reservoir, for example to a syringe, and the outlet of the micropump is linked to a vacuum pump : starting up the latter causes aspiration of the air of the micropump and injection of fluid. A second technique consists of using an enclosure connected to a vacuum pump and partially filled with fluid. After plunging the micro-pump in the fluid, the vacuum pump is activated to remove air from the enclosure and then the pressure in the enclosure is increased by re-introducing air, thereby forcing the fluid into the micropump. This operation is repeated several times to ensure that sufficient air has been expelled from the micropump. It will be understood that these two techniques need a considerable amount of equipment and that they cannot therefore be carried out in a doctor's surgery, but only in a hospital environment or in a factory, during manufacture.

The micropump may also be primed under normal atmospheric pressure. Fluid is simply injected into the micropump using a syringe by means of successive strockes or continuously. Air is normally driven by the fluid or carried therewith towards the outlet of the micropump. Nevertheless, due to the shape of the pump chamber and of the channels of the micropump, air bubbles could form and remain trapped in the micropump. This risk can be reduced by increasing the pressure at which the fluid is injected. Nevertheless the elimination of the air bubbles remains largely unreliable.

SUMMARY OF THE INVENTION

It is an object of the invention to provide a micropump which can be primed more safely and more reliably.

The object of the invention is therefore a micropump of the type comprising a first wafer and at least a second wafer bonded to the first wafer, which together define a pump chamber, at least one upstream valve to selectively connect the pump chamber with at least one inlet of the micropump and at least one downstream valve to selectively connect the pump chamber with at least one outlet of the micropump, this micropump also comprising means for causing a periodic variation in the volume of the pump chamber, said micropump being characterized in that at least one upstream valve has a membrane defining an upstream compartment and a dowstream compartment, the membrane being pierced by an orifice for the passage of a fluid from one compartment to the other and a sealing ring surrounding said orifice, designed by virtue of a resilient constraint, normally to bear against one valve seat provided on a wafer facing said ring, the orifice being so positioned that, during the priming of the micropump, the fluid entering the downstream compartment attains a determined and unique part of the peripheral wall of the downstream compartment before reaching any other part of this peripheral wall.

Thanks to this structure all of the air is effectively forced downstream. Although the propagation of the fluid in the downstream compartment has not been accurately observed due to the speed of flow of the fluid, the hypothesis is proposed that the fluid entering the downstream compartment during the priming of the micropump first reaches to peripheral wall in this part by driving the air on both sides thereof and then towards the outlet passage.

It is preferred that the height of the upstream compartment of each downstream valve which communicates directly with the pump chamber is less than 40 $\mu$m. The height of this compartment is thus sufficiently low for any air contained therein to be evacuated from the valve when the fluid is injected into the micropump.

In numerous applications of the micropump of the invention, notably in the medical field, the fluid is an aqueous solution. In this case it has been found that evacuation of air from downstream compartment is facilited if the surfaces of the wafers are rendered hydrophilic and it is assumed that this results from the fact that the fluid, after having reached that part of the wall which is closed to the orifices, forms a wave front which adheres to the wall and propagates towards the outlet passage by driving the air out in front of it.

The micropump may have one or more valves according to the invention between the inlet of the micropump and the pump chamber and between the pump chamber and the outlet of the micropump. It is particularly advantageous that each upstream valve communicating directly with the pump chamber is in accordance with the invention to ensure the absence of air from the pump chamber.

BRIEF DESCRIPTION OF THE DRAWING

The characteristics and advantages of the invention are better illustrated by the following description of embodiments of the invention given for purposes of example but which are not limiting with reference to the enclosed drawings, in which.

DETAILED DESCRIPTION OF THE INVENTION

Figure 1:
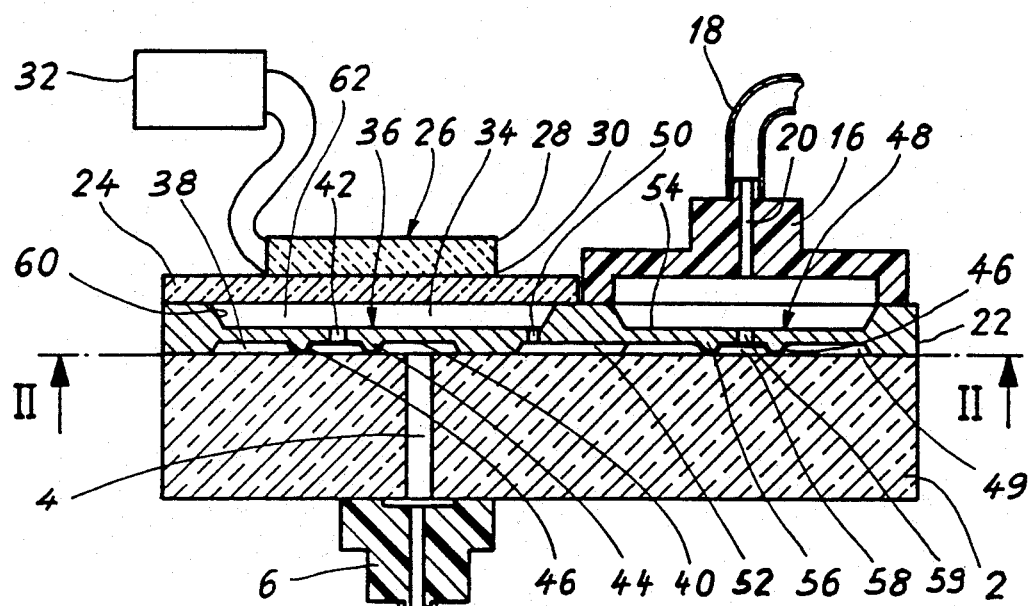
FIG. 1 is a schematic section of a micropump of the invention.

In the drawings, the same element shown on several figures bears in each case the same reference numeral. In the embodiments to be described, the micropump is provided with an inlet valve and an outlet valve. It should nevertheless be noted that the invention also applies to micropumps having several valves arranged between the inlet and the pump chamber and/or several valves arranged between the pump chamber and the outlet. The micropump may also be provided with a plurality of inlets and a plurality of outlets.

Figure 2:
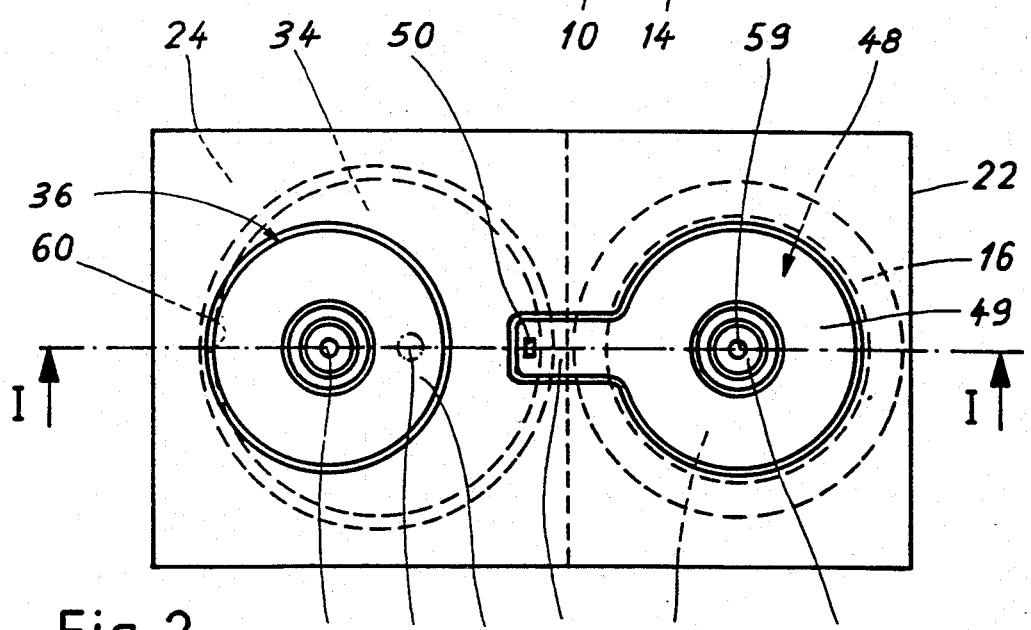
FIG. 2 is a top view of the intermediate wafer of the micropump shown in FIG. 1.

Reference will first be made to FIGS. 1 and 2 which show a first embodiment of the micropump according to the invention.

It should be noted that, for sake of clarity, the thicknesses of the various wafers comprising the micropump have been greatly exaggerated in the drawings.

The micropump of FIGS. 1 and 2 comprises a base wafer 2 of, for example, glass, which is pierced by a channel 4 forming the inlet channel of the pump. This channel 4 communicates with a connection 6 connected to a tube 8 which is in turn connected to a reservoir 10 containing the liquid substance to be pumped. The reservoir is closed by a pierced cap 12, a mobile piston 14 separating the working volume of the reservoir 10 from the exterior. This reservoir may contain a medicament, for example if the pump is used to inject a precise dosage of this medicament into the human body. In this application the micropump may be worn on the body of the patient, or implanted therein.

The outlet of the micropump is provided with an outlet connection 16 which can be connected to an injection needle (not shown) by a tube 18. In the embodiment described this outlet connection 16 is fixed to another wafer 22 which will be described bellow.

The use in this manner of the micropump of the invention is particularly suitable for treating certain forms of cancer with peptides, where medication is preferably given in a precise dosage and the doses are repeated at regular intervals in small amounts. Another possible application is for the treatment of diabetics who need to receive regular, small doses of medicament in the course of the day, it being possible for example to determine the dosage by means known per se, measuring the blood sugar level and automatically controlling the pump so that a suitable dose of insulin can be injected.

The wafer 22 of silicon or other material capable of being machined using photolithographic etching technology is bonded to the glass wafer 2. Above this silicon wafer is a glass closure wafer 24, the thickness of which is such that it can be deformed by a control element 26 which, in the embodiment of the invention described herein, is a piezoelectric disc provided with electrodes 28 and 30 connected to an alternating current generator 32. This disc may be that manufactured by Philips under the reference number PXE-52 and may be bonded to the wafer 24 using a suitable adhesive.

For purposes of example, the intermediate silicon wafer 22 can have a <100> crystalline orientation so as to render it suitable for etching and to give it the required strength. The wafers 2, 22 and 24 are preferably well polished. These wafers 2, 22, 24 are advantageously renderer hydrophilic, particularly if the fluid used in the micropump is an aqueous solution. For this purpose the silicon wafer 22 may be immersed into boiling $HNO_3$.

The wafers 22 and 24 together define first of all a pump chamber 34 (see also FIG. 2) for example circular in shape, this chamber being situated below an area of the wafer 24 which can be flexed by the control element 26.

A first check valve 36 machined out of the silicon wafer 22 is interposed between the inlet channel 4 and the pump chamber 34.

This first valve 36 comprises two compartments, an upstream compartment 38 and a downstream compartment 62, this latter also serving as the pump chamber 34 in the embodiment shown. The two compartments are separated by a membrane 40 substantially circular in shape and pierced at its centre by an orifice 42 and provided, on the side of the channel 4, with an annular rib 44 which surrounds the orifice 42 and constitutes a sealing ring.

This sealing ring 44 is covered by a thin oxide layer 46 also obtained using photolithographic technology which subjects the membrane 40 to a certain degree of pre-tension causing the top of the sealing ring 44 to bear against the glass wafer 2, the latter thus acting as seat for the valve 36.

The membrane 49 and/or the sealing ring 44 could of course be other than circular in shape, for example oval, rectangular or square. Though the sealing ring is, in this embodiment, preferably provided on the membrane, it is obvious that in same occasions the sealing ring could also be machined in the glass wafer facing the membrane.

The channel 20 of the outlet connection 16 of the pump communicates with the pump chamber 34 through a valve 48 of similar design to the valve 36.

The valve 48 thus comprises a membrane 54 and an annular rib or sealing ring 56 covered by an oxide layer 46 which defines a volume 58 communicating by an orifice 59 with the channel 20 and an upstream compartment 49. This latter communicates directly with the pump chamber 34 through an orifice 50 and a channel 52, both machined in the silicon wafer 22.

The operation of this micropump is similar to that of the two-valve micropump described in the above mentioned article by H. van Lintel et al.

By way of example, the thickness of the wafers 2, 22 and 24 may be about 1 mm, 03. mm and 0.2 mm respectively for a surface area of the wafers of the order of 15 by 20 mm.

Moreover, the wafers may also be fixed to one another using various conventional bonding technologies such as adhesion or, for example, the technology known as anodic bonding.

During priming of the micropump it is important that no air bubble of any substantial size remains in a volume communicating directly with the pump chamber, since this would jeopardize the functioning of the micropump. It may be considered that a volume of air of about less than one tenth of the volume pumped at each pumping cycle does not significantly impair the working of the micropump. In practice, this means that no air bubble may be visible to the naked eye.

For this purpose and in accordance with the invention, the valve 36 located in front of the pump chamber has a special structure which will now be described.

The orifice 42 of the valve opens into the downstream compartment which, in this embodiment, is also the pump chamber, at a point relatively close to the part 60 of the wall of the downstream compartment and relatively distant from the orifice 50. More specifically, the distance between the orifice 42 and the part 60 of the peripheral wall is smaller than the distance between the orifice and any other part of the peripheral wall of the downstream compartment.

When, as in the embodiment shown, the orifices 42 and 50 are arranged on a symmetrical axis of the downstream compartment, the part of the peripheral wall of the downstream compartment closest to the orifice 42 is also on this axis of symmetry. Nevertheless it is conceivable that, for certain shapes of the downstream compartment, the part of the peripheral wall of the downstream compartment nearest to the orifice 42, the orifice 42 and the orifice 50 will not be aligned.

What is important is that the location of the orifice 42 is such that, when the fluid spreads in the downstream compartment during the priming of the micropump, the first contact between the fluid and the wall of this compartment occurs in a unique and specific part of this wall.

Figure 12:
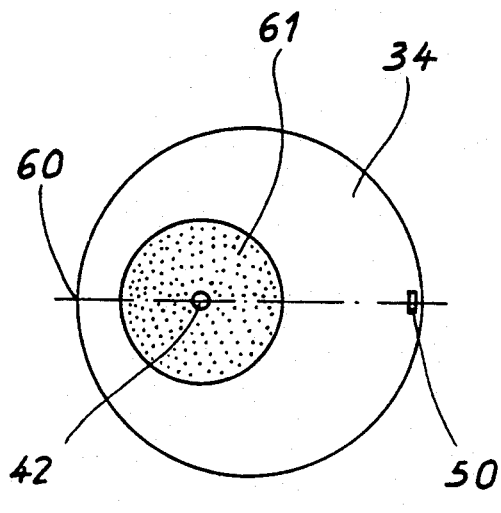
Figure 12:
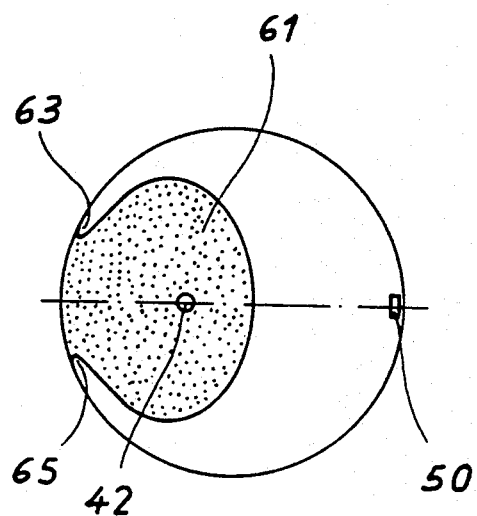
Figure 12:
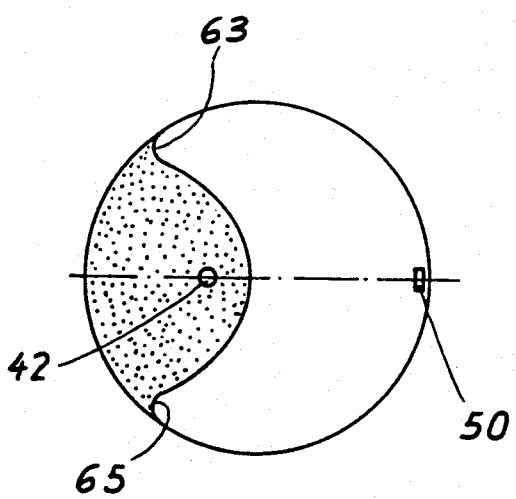
Figure 12:
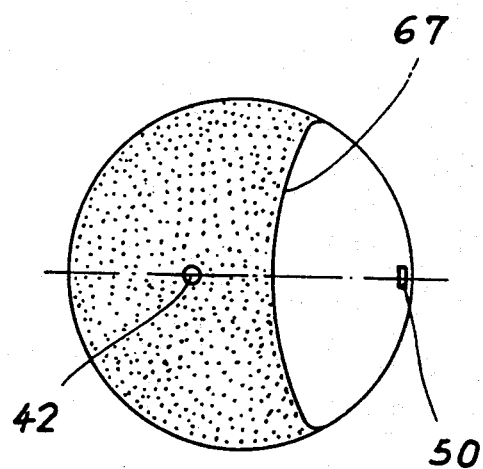

FIGS. 12a to 12d show how it is believed that the fluid spreads in the downstream compartment of the valve in the case of an aqueous fluid and a compartment having hydrophilic walls. To begin with a drop of fluid 61 is formed that is substantially circular and centered on the orifice 42 (FIG. 12a). When this drop reaches the wall of the compartment (FIG. 12b), in the part 60 closest to the orifice 42, the edges 63 and 65 of the drop of fluid progress rapidly by capillarity along the compartment wall, on both sides of the part 60 (FIG. 12c). A wave front 67 is thus formed which advances towards the orifice 50, pushing the air away ahead of it (FIG. 12d).

In contradistinction hereto, in the micropumps of the prior art, the downstream compartment is generally in the shape of a disc and the orifice 42 is in the center, along the axis of symmetry. During the priming of the micropump, the drop of fluid extending from the orifice 42 can thus reach the peripheral wall of the compartment at an indefinite location or simultaneously at several indefinite locations, causing the formation of air bubbles along the peripheral wall of the downstream compartment.

As may be seen in FIGS. 1 and 2, the orifice 50 is provided in the path of the downstream compartment 62 opposite the part 60 and in immediate proximity to the peripheral wall of this downstream compartment. This orifice 50 opens out into the channel 52. The wave front formed in the downstream compartment 62 thus propagates across the orifice 50 and progresses in the channel 52 pushing all the air away ahead of it.

The structure according to the invention makes it possible to evacuate the air from the downstream compartment 62, that is from the pump chamber 34, and from the orifice 50 of the micropump shown in FIGS. 1 and 2, which greatly improves the priming of the micropump. Nevertheless, some of the air can remain trapped in the upstream compartment 49 of the valve 48. It is possible to improve the evacuation of air from this upstream compartment by restricting its height to a sufficiently low value. A height of less than 40 $\mu$m has been found to give satisfactory results.

The following hypothesis is advanced to explain the evacuation of the air from the upstream compartment 49 of the valve 48. The small height of this compartment imparts a high speed on the fluid; as a result a substantial part of the fluid surrounds the sealing ring 56 when the valve is open and pushes the air across this orifice. As a result, perhaps all that remains are one or more small air bubbles in the upstream compartment 49 which are easily driven by friction with the fluid towards the orifice 59, thanks to the high speed of the fluid.

Other factors can contribute to good evacuation of the air. A homogenous height of the compartments avoids air bubbles to form and remain trapped in the convolutions or recesses of the compartments. It has also been found that placing the micropump in vertical position during the initial filling, with the orifice 42 lower than the orifice 50, facilitates the migration of the air towards the orifice 50.

Air bubbles may also be formed in the upstream compartment 38. To avoid this, it is also advantageous for the height of this compartment to be homogenous and, in addition, for this height to be less than 40 $\mu$m.

In this way a micropump is finally obtained from which it is possible to evacuate the air from the pump chamber and from all other compartments of the micropump in a simple way.

By way of example, the upstream compartments 38 and 49 can have a diameter of 4 mm for a height of 30 $\mu$m, orifices 42 and 50 diameter of 300 $\mu$m and the downstream compartment 62 a diameter of 8 mm and height of 200 $\mu$m.

It should be noted that it is not absolutely essential for all the air bubbles to be evacuated from the upstream compartment 62 of the valve 36; the micropump even works if there are air bubbles in this upstream compartment inasmuch as they remain trapped therein and are not driven into the downstream compartment. In contradistinction hereto, it is important that no air bubble remains in the downstream compartment or, more precisely, that the volume of air remaining is sufficiently small, as mentioned above, so as not to jeopardize the correct operation of the micropump.

Figure 3:
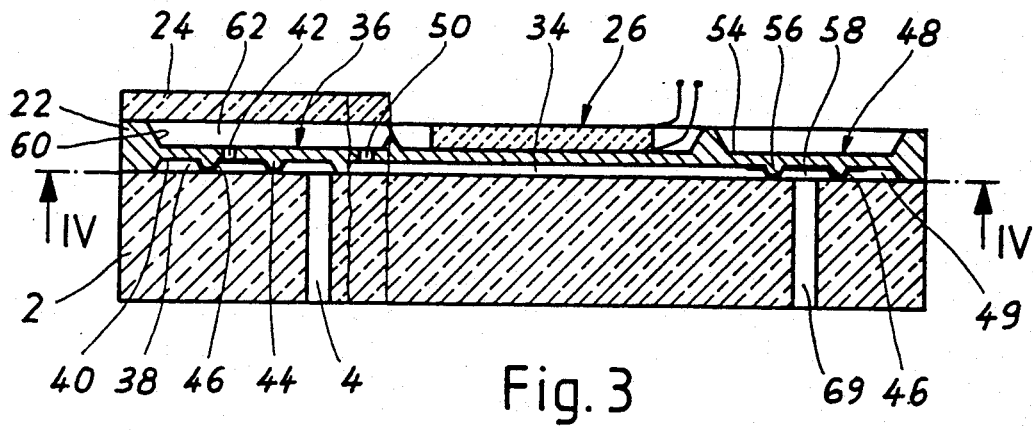
FIG. 3 is a schematic section of another micropump of the invention.
Figure 4:
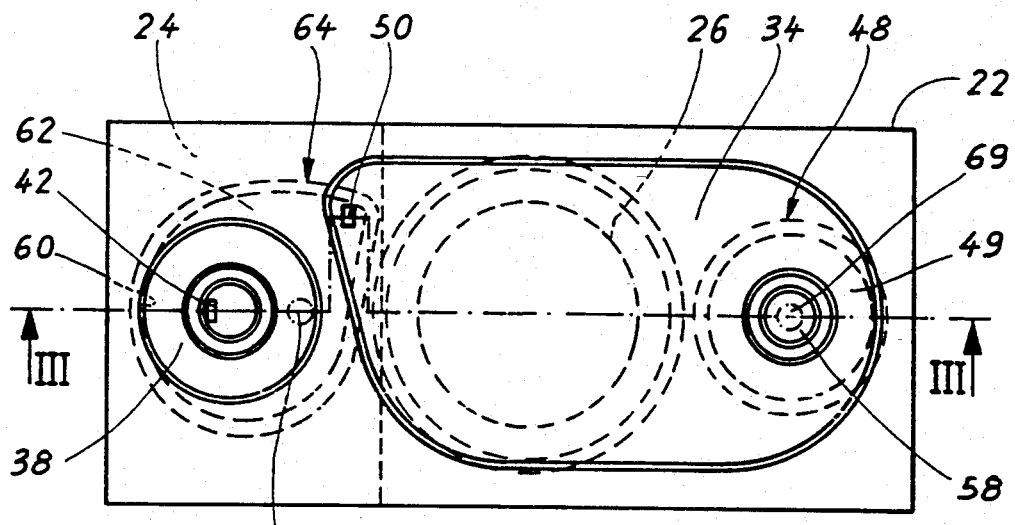
FIG. 4 is a top view of the intermediate wafer of the micropump shown in FIG. 3.

In the embodiment shown in FIGS. 1 and 2, the downstream compartment also serves as the pump chamber. It is of course possible to separate these two zones. A micropump according to an embodiment of this type is shown in FIGS. 3 and 4. For purposes of simplification, only the three wafers and the control element have been shown.

As shown in FIG. 3, the inlet valve 36 arranged upstream from the pump chamber 34 comprises an upstream compartment 38 and a downstream compartment 62, this latter communicating with the pump chamber 34 by an orifice 50. It will be noted that in this embodiment the control element 26 is fixed onto the silicon wafer 22 and that the membrane 54 of the outlet valve 48 has no orifice, the outlet channel 69 of the micropump being made in the plate 2 opposite the sealing ring 56.

With this outlet valve, the outlet pressure only acts, when the valve 48 is closed, on the small surface of the volume 58 compared to the substantially greater surface on which the pressure prevailing in the pump chamber is able to act. This results in regulation of the outlet output which becomes virtually independent of the outlet pressure, this effect being brought about by the pre-tension ensured by the oxide layer 46.

The upstream compartment 38 is in the form of a disc, as in the embodiment shown in FIGS. 1 and 2, whereas the downstream compartment 62 also substantially circular in shape has a part 64 that is substantially V-shaped at the base of which is disposed the orifice 50 communicating with the pump chamber. This V-shaped part 64 makes it possible to guide the air towards the orifice 50 more effectively.

The orifice 42 that communicates with the two compartments has a rectangular section and is eccentrically located with respect to the sealing ring so as to be as close as possible to the part 60 of the peripheral wall of the downstream compartment 62.

In each of the embodiments shown in FIGS. 1-2 and 3-4 it will be noted that the distance between the orifice 42 of the valve at the wall of the downstream compartment increases in continous manner going from the part 60 of the wall which is closest to the orifice 42, towards the part of the wall closest to the orifice 50. This shape ensures that no air bubble can be trapped against the wall. In the case of a hydrophilic fluid, the shape of the downstream compartment is less important, but a shape such as that mentioned above nevertheless remains preferable.

It is of course important that the air expelled from the downstream compartment of the valve 36 does not remain in the pump chamber or in the outlet valve chamber 48 which communicates with the pump chamber.

Figure 5:
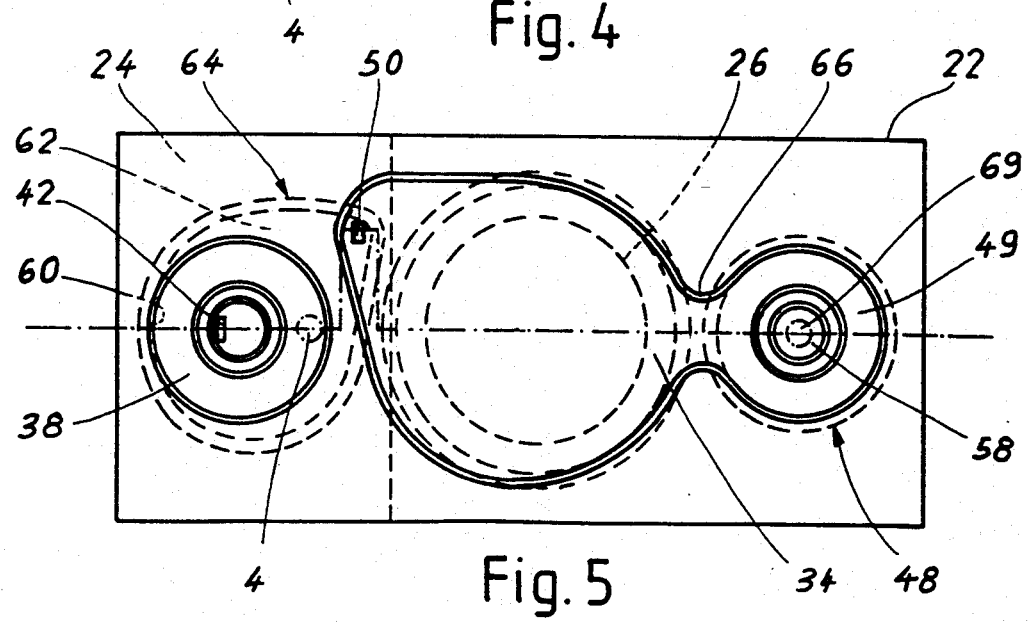
FIG. 5 is a modification of the embodiment of the wafer shown in FIG. 4.

In FIG. 2, the orifice 50 of the outlet of the downstream compartment opens into a channel 52 which leads to the valve compartment 48. In FIG. 4 the outlet valve 48 is directly placed in the pump chamber. FIG. 5 illustrates another variation of the embodiment of FIG. 4 in which a bottleneck 66 defines a channel separating the pump chamber 34 and the valve compartment 48.

In these three embodiments it will be noted that the orifice 50 is located in proximity to a wall. This makes it possible to drive the air in the opposite direction, that is towards the valve 48, in the same way as, in the downstream compartment, the air is driven towards the orifice 50 by the position of the orifice close to the wall 60.

Figure 6:
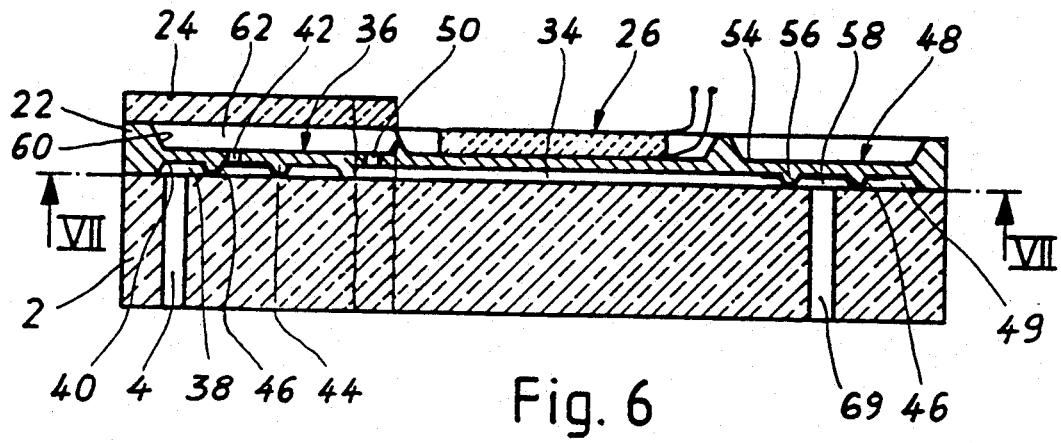
FIG. 6 is a schematic section of an embodiment of the micropump shown in FIG. 3.
Figure 7:
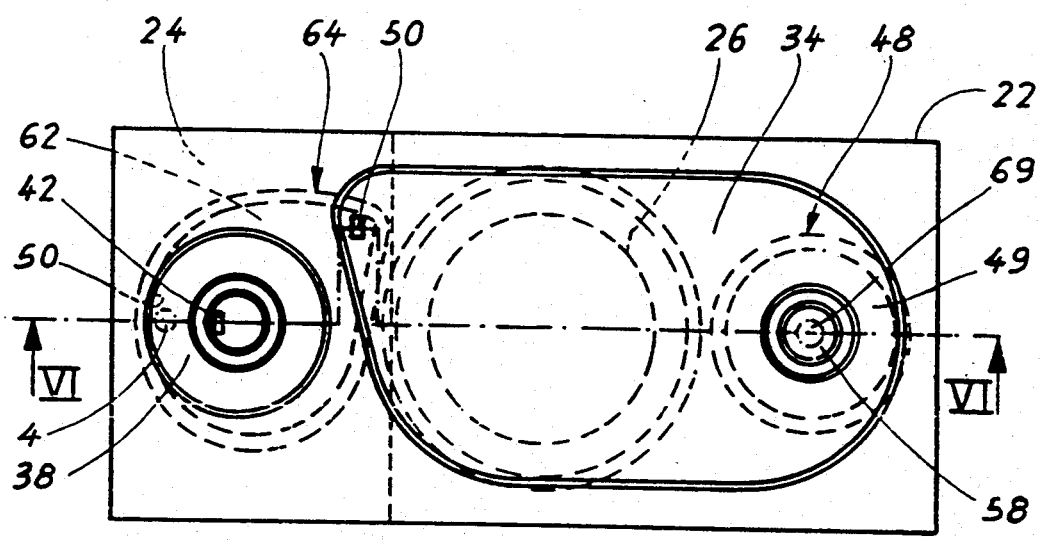
FIG. 7 is a top view of the intermediate wafer of the micropump shown in FIG. 6.

In the embodiments of FIGS. 1-5, it also will be noted that orifices 42 and 50 are on opposite sides of the inlet channel 4. FIGS. 6 and 7 illustrate a currently preferred embodiment of the micropump shown in FIGS. 3 and 4. In this embodiment the position of the inlet channel 4 is different with respect to the orifices 42 and 50.

Indeed, it appeared that an air bubble located in the upstream compartment 38 of the inlet valve 36 of the micropump shown in FIGS. 3 and 4 after initial priming of the micropump which, in itself, is not disturbing provided this air bubble remains in this compartment could, in some cases become trapped in the downstream compartment 62 after it has been driven by the fluid across the orifice 42.

This is because, under laminar flow and after the initial priming of the micropump, the speed of the fluid flowing into the downstream compartment 62 of the inlet valve 36 is not the same in all directions. Indeed, it is conceivable that this speed is substantially highest in the direction of the orifice 50 (normal direction of flow of the fluid) and that it is substantially weaker, or negligible, in the opposite direction.

An air bubble which could be formed in the upstream compartment 38 would appear in the most distant part away from the inlet channel 4. Were this air bubble driven by the fluid across the orifice 42, it would be driven into a part of the downstream compartment where the speed of the fluid is negligible; the air bubble could then remain trapped in the downstream compartment.

Figure 8:
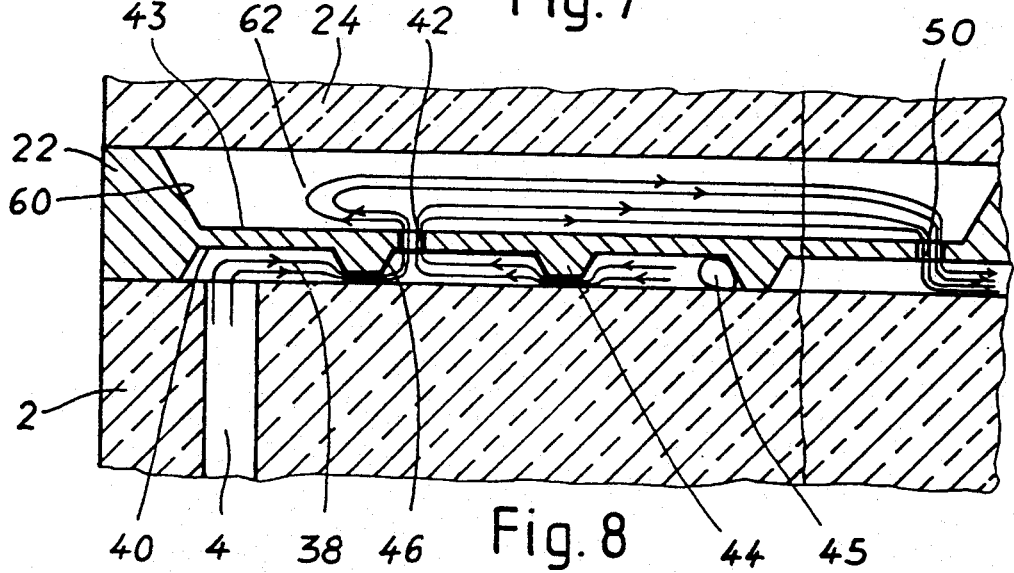
FIG. 8 is a schematic enlarged section of part of the micropump shown in FIG. 6.

This risk is strongly reduced in the micropump shown in FIGS. 6 and 7. FIG. 8, which shows the inlet valve in enlarged form, illustrates how an air bubble can be driven by the fluid.

This figure shows the flow lines of the fluid under laminar flow condition, i.e. in the normal state of operation of the micropump after its initial priming. This flow is substantial between the orifices 42 and 50 and much less or negligible, in the opposite region 43 of the downstream compartment.

If the inlet channel 4 is placed opposite this region 43, as is the case in FIG. 8, an air bubble 45 could only be formed in the upstream compartment 38 of the valve 36 in the region opposite that into which the inlet channel 4 comes out. When it is driven by the fluid, it follows the flow lines and will thus automatically end up in the region located between the orifices 42 and 50 where the flow is highest, in such a way that it will not remain trapped in the downstream compartment 62 of the valve 36.

The inlet channel 4 of the micropump shown in FIGS. 1 and 2 can also be moved to another place as shown in FIG. 8. Generally speaking, a structure of this type is useful in micropumps of which the upstream valve compartment is sufficiently small for the air bubbles to be driven by friction with the fluid.

Figure 9:
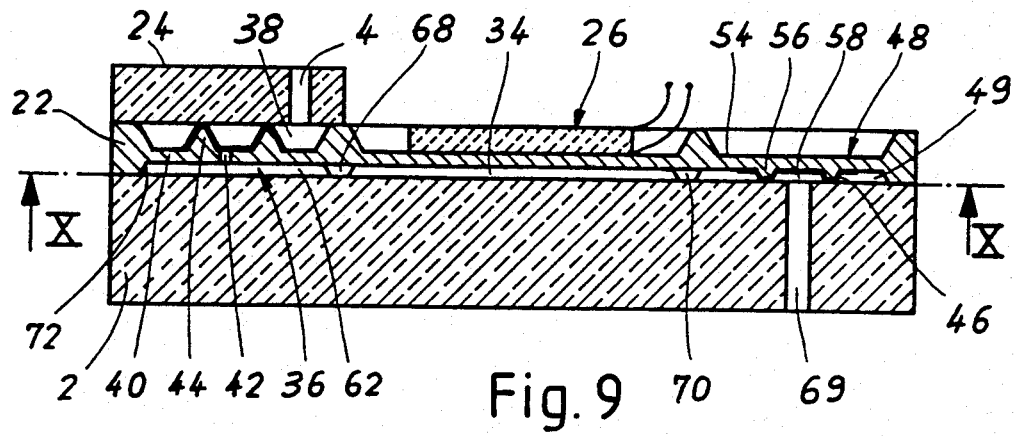
FIG. 9 is a schematic section of another micropump of the invention.
Figure 10:
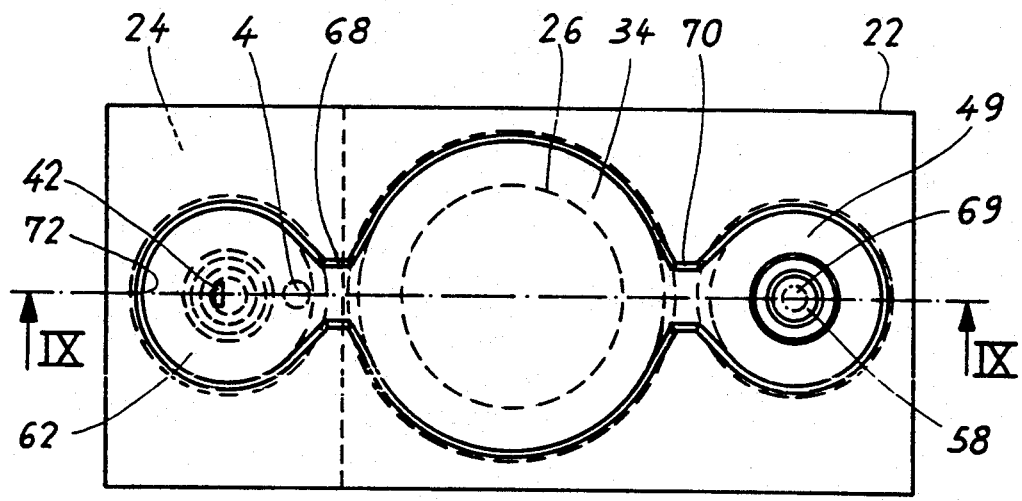
FIG. 10 is a top view of the intermediate wafer of the micropump shown in FIG. 9.

FIGS. 9 and 10 show another embodiment of the micropump of the invention.

As may be seen in FIG. 9, the channel 4 forming the inlet channel is pierced in the wafer 24 whereas the channel 69 forming the outlet channel remains pierced in the wafer 22. The sealing ring 44 of the inlet valve 36 is thus formed on the face of the membrane 40 facing wafer 24. In this way, the downstream compartment 62 of the inlet valve 36 communicates downstreams with the pump chamber 34, by a channel 68. In symmetrical manner, a channel 70 is provided between the pump chamber 34 and the compartment of the outlet valve 48.

The width of these channels 68 and 70 may be increased up to the dimension of the pump chamber 34.

Figure 11:
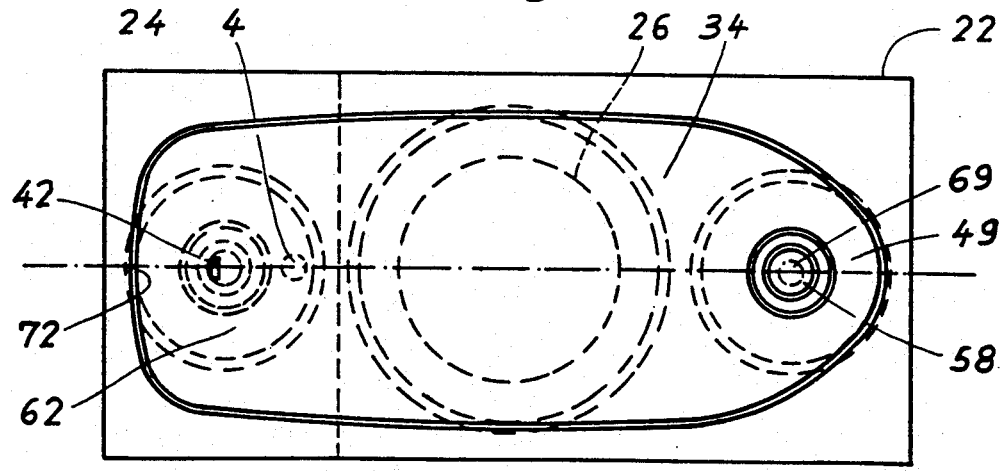
FIG. 11 is an embodiment of the wafer shown in FIG. 10, and FIGS. 12a to 12d illustrate the propagation of the fluid in the downstream compartment of a valve of a micropump according to the invention.

One then obtains, as shown in FIG. 11, a single volume forming the downstream compartment of the inlet valve 36, the pump chamber and the compartment of the outlet valve 48.

What is claimed is:

1. A micropump comprising:
   a first wafer;
   at least a second wafer bonded to the first wafer to define a pump chamber;
   at least one upstream valve to selectively connect the pump chamber with at least one inlet of the micropump, said upstream valve having a membrane defining an upstream compartment and a downstream compartment, said membrane being pierced by an inlet orifice for the passage of a fluid from one compartment to the other and by an outlet orifice communicating with said downstream compartment, and said downstream compartment being surrounded by a peripheral wall having a nearest part, an intermediate part and a remotest part relative to said inlet orifice;
   at least one downstream valve to selectively connect the pump chamber with at least one outlet of the micropump;
   control means for causing a periodic variation in the volume of said pump chamber; and,
   a sealing ring surrounding said inlet orifice and resiliently biased to bear against a valve seat facing said ring;
   said inlet orifice being positioned in the proximity of said nearest part of the peripheral wall so that, during priming of the micropump, the fluid entering the downstream compartment reaches first said nearest part before being led by said intermediate part to said remotest part of the peripheral wall, said outlet orifice being positioned in the proximity of said remotest part of the peripheral wall.

2. A micropump according to claim 1 wherein the inlet and outlet orifices are positioned on opposite sides of the micropump inlet.

3. A micropump according to claim 1 wherein said downstream valve includes an upstream compartment, and the height of the upstream compartment of at least one of said upstream and downstream valves is less than 40 μm.

4. A micropump according to claim 1 wherein said outlet orifice comes out downstream into a volume defined by another peripheral wall having a part nearest said outlet orifice, said outlet orifice being positioned in such a manner that, during the priming of the micropump, the fluid entering said volume reaches first the nearest part of said other peripheral wall before reaching any other part of said other peripheral wall.

5. A micropump according to claim 1 wherein the downstream compartment constitutes said pump chamber.

6. A micropump according to claim 1 wherein said downstream compartment and said pump chamber are in different planes and communicate via said outlet orifice.

7. A micropump according to claim 1 wherein a single volume forms the downstream compartment of said upstream valve, the pump chamber and a compartment of said downstream valve, and wherein an outlet passage is defined by said downstream valve.

8. A micropump according to claim 1 wherein said downstream compartment comprises an outlet passage formed by a channel substantially disposed in a zone furthest away from said nearest part.

9. A micropump according to claim 1 wherein an upstream compartment of said downstream valve is in direct communication with the pump chamber and has a height of less than 40 μm.

10. A micropump according to claim 9 wherein the height of the upstream compartment of said upstream valve is less than 40 μm.

11. A micropump according to claim 1 wherein the distance between the inlet orifice and the peripheral wall of the downstream compartment increases in a direction along this wall away from said nearest part.

12. A micropump according to claim 1 wherein the surfaces of the portions of said wafers for contacting the fluid are hydrophilic.

13. A micropump according to claim 12 wherein the first wafer is made of silicon and said surfaces of the first wafer are rendered hydrophilic by oxidation, and wherein the second wafer is made of glass.

14. A micropump according to claim 1 in which, after priming of the micropump, the fluid flow is laminar in the downstream compartment of the upstream valve, the speed of flow being relatively high in one region of said downstream compartment and relatively low i another region of said downstream compartment, and wherein said micropump further comprise an inlet channel to bring the fluid into the upstream compartment of the upstream valve, said inlet channel substantially facing said other region of said downstream compartment.

15. A micropump according to claim 1 wherein said sealing ring is integral with said membrane.

* * * * *